United States Patent [19]

Riehl et al.

[11] Patent Number: 4,629,989
[45] Date of Patent: Dec. 16, 1986

[54] PATIENT ALIGNMENT SYSTEM FOR NMR STUDIES

[75] Inventors: Mark E. Riehl, Waukesha; Robert J. Dobberstein, West Allis, both of Wis.

[73] Assignee: General Electric Company, Milwaukee, Wis.

[21] Appl. No.: 550,704

[22] Filed: Nov. 10, 1983

[51] Int. Cl.[4] ............................................. G01R 33/20
[52] U.S. Cl. ...................................... 324/318; 324/300
[58] Field of Search ............... 356/375, 376; 364/561, 364/414, 572, 574; 378/901, 20, 117; 324/307, 309, 312, 313, 314, 318, 300; 128/653

[56] References Cited

U.S. PATENT DOCUMENTS

| | | | |
|---|---|---|---|
| 2,133,241 | 5/1938 | Baker | 356/375 |
| 3,164,661 | 1/1965 | Dellon | 364/414 |
| 3,423,592 | 1/1969 | Selgin | 356/375 |
| 3,594,783 | 7/1971 | Bullock | 364/561 |
| 3,983,399 | 9/1976 | Cox, Jr. | 364/414 |
| 4,117,337 | 9/1978 | Staats | 41/16 |
| 4,242,587 | 12/1980 | Lescrenier | 378/20 X |
| 4,307,343 | 12/1981 | Likes | 324/307 |
| 4,339,716 | 7/1982 | Young | 324/309 |
| 4,354,499 | 10/1982 | Damadian | 324/309 |

Primary Examiner—Stephen A. Kreitman
Assistant Examiner—Scott M. Oldham
Attorney, Agent, or Firm—Alexander M. Gerasimow; Douglas E. Stoner

[57] ABSTRACT

A patient alignment system utilizes stationary and mobile light fan beams for precisely positioning a patient for performing NMR studies. One assembly of preferably laser light sources is utilized to create a visible reference point for aligning a patient anatomical reference in the staged scan position. The reference position is then used as a reference to locate the scan volume and to automatically translate the patient so that the scan volume is in the optimum homogeneous region of the polarizing magnetic field. Two laser assemblies, each separately operable to provide a vertically movable laser fan beam, are used to locate a vertical reference point. The vertical reference point is used to retrospectively reconstruct images centered in the field of view. The vertical reference point is used to obtain prospectively image data to reconstruct magnified zoom or unmagnified images offset from the isocenter.

10 Claims, 8 Drawing Figures

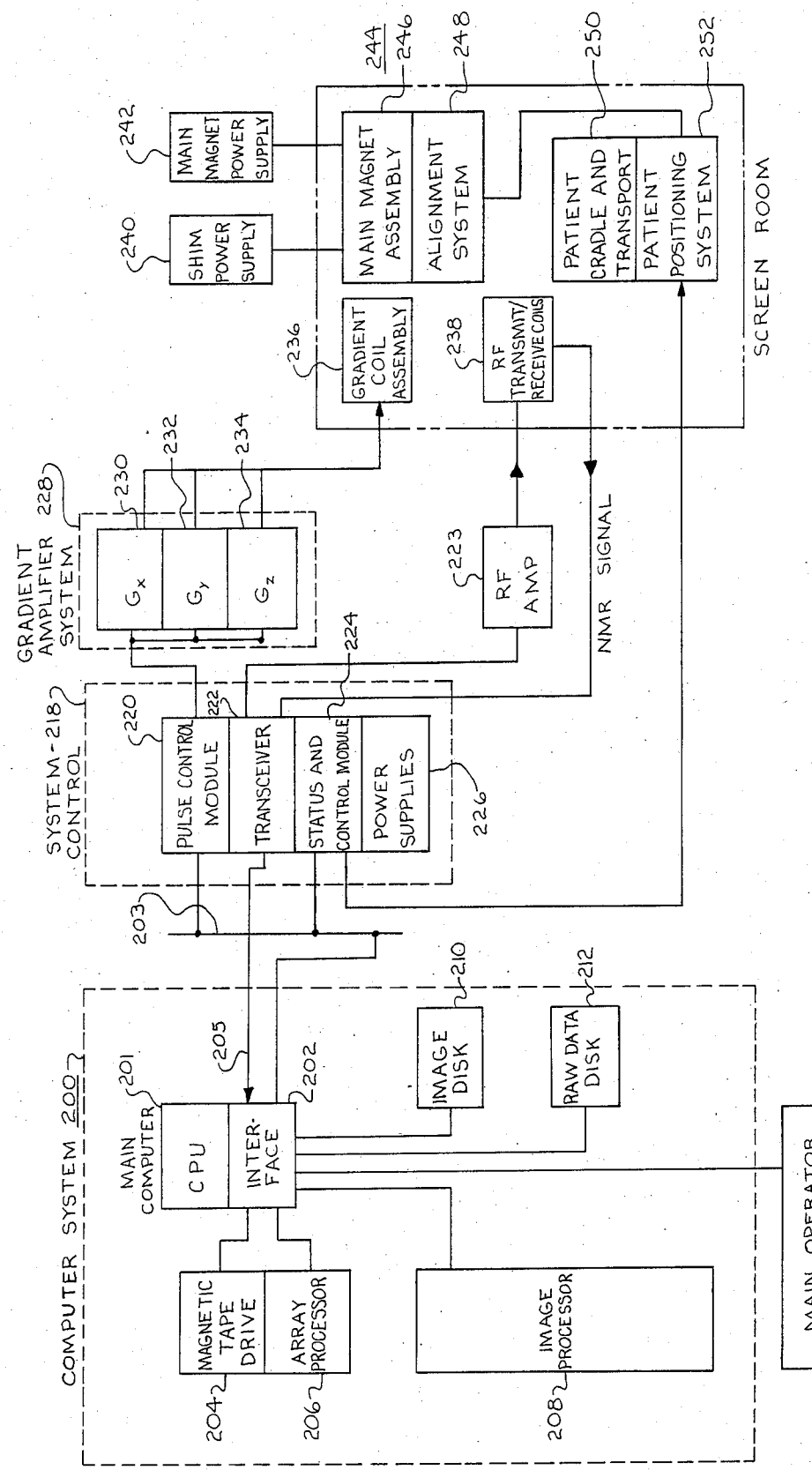

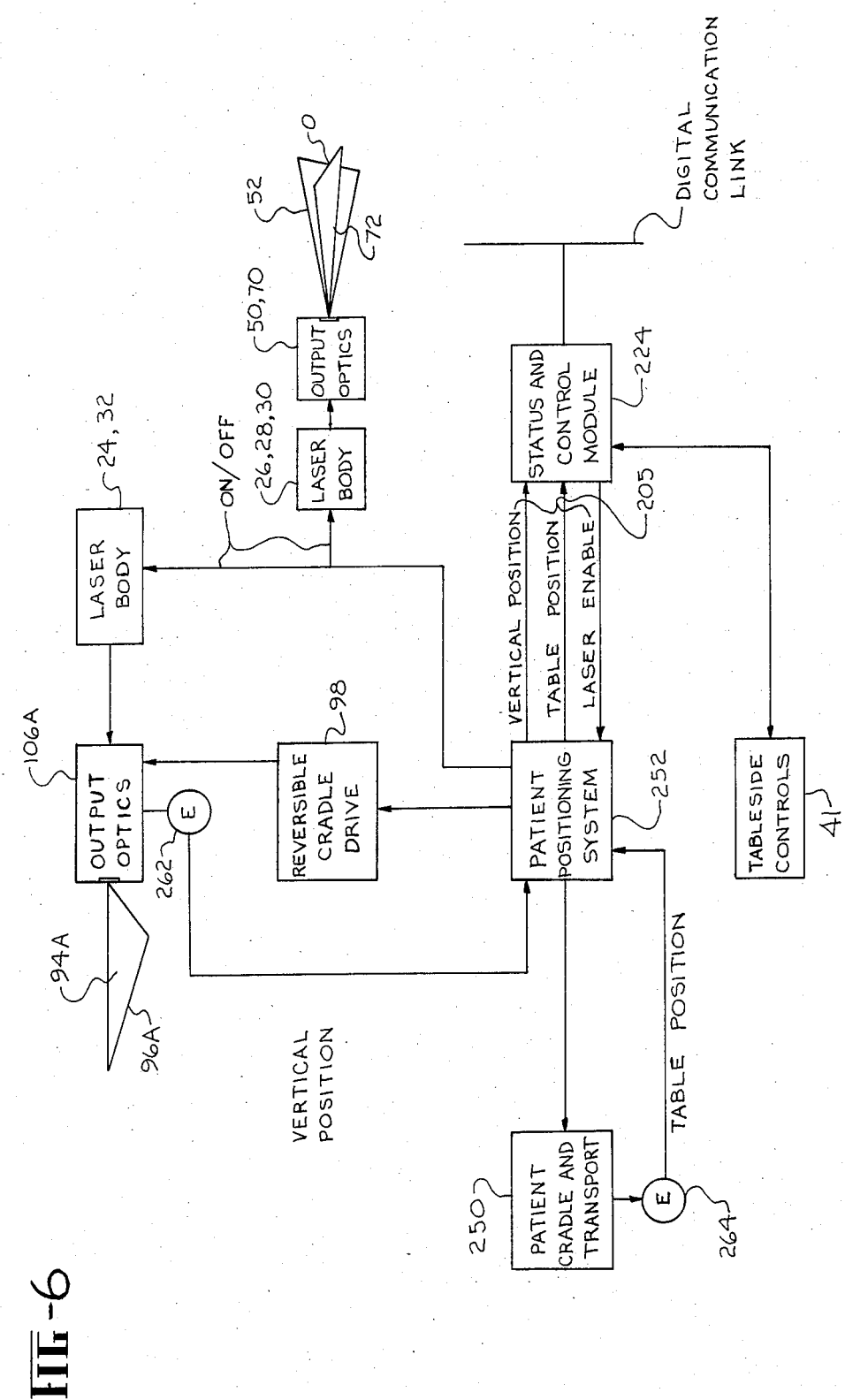

PATIENT ALIGNMENT SYSTEM FOR NMR STUDIES

BACKGROUND OF THE INVENTION

This invention relates to NMR systems. More specifically, the invention relates to a system for precisely aligning a patient on a table prior to performing an NMR study and for providing reference data useful in acquisition of NMR data and in image manipulation.

An NMR system typically is made up of a magnet, a table for supporting a patient, and digital computer apparatus for controlling system operation, data acquisition, and subsequent image reconstruction, for example. The magnet, which may be of resistive or superconductive construction, is generally configured as a cylinder having a longitudinal bore approximately 90 cm. in diameter. A shim coil assembly located within the bore is used to correct magnetic field inhomogeneities in the main field. A gradient coil system with a typical diameter of about 65 cm. is situated within the magnet bore interiorly of the shim coil assembly. Gradient coils are needed in NMR imaging systems to provide substantially linear magnetic-field gradients used to encode spatial information into NMR signals. A radio-frequency (RF) body coil used for exciting the nuclear magnetic resonance phenomenon and for receiving NMR signals further limits useful bore diameter to approximately 55 cm. This is sufficient for accommodating most patients, but severely limits the ability to move the patient both transversely and vertically within the bore.

To obtain optimal NMR image quality, the patient region of interest must be positioned within a centered spherical volume of approximately 40 cm. in diameter centered about a system isocenter where the magnetic field produced by the magnet is most homogeneous. This is accomplished by using a patient support device capable of bidirectional longitudinal travel within the magnet bore but which does not travel in the transverse or vertical directions. The use of such a device has its design advantages since transverse travel is severely restricted in any case by the RF body coil diameter. Vertical travel is not only limited, but is difficult to implement because of the extreme longitudinal travel range (about 300 cm.) and the requirement that the patient support system be capable of supporting a 300 pound load. A problem which arises due to the lack of vertical travel capability (i.e., without the ability to center the patient volume of interest with the isocenter) is that the image reconstruction process lacks the necessary reference information to an image center for the purpose of displaying images centered in the field of view or for reconstructing magnified and unmagnified images which are offset from the image center. The manner in which offset images are reconstructed is claimed and disclosed in copending, commonly assigned U.S. patent application Ser. No. 555,097 now U.S. Pat. No. 4,593,247, filed by Gary H. Glover, which is incorporated herein be reference.

It is therefore an object of the present invention to provide a patient alignment system for precisely positioning a patient longitudinally in a region of interest within the magnetic field volume having optimum homogeneity.

It is another object of the invention to provide a patient alignment system capable of providing reference information for displaying centered images even when the region of interest is not centered with the isocenter.

It is a further object of the invention to provide a patient alignment system for referencing an anatomical reference point which is recorded and which may then be used as a reference for determining the dimension and position of the region to be studied.

SUMMARY OF THE INVENTION

A patient alignment system is useful with an NMR system for acquiring NMR data in the course of an NMR scan of a predetermined patient volume. The NMR system includes a magnet which produces a polarizing magnetic field within the magnet bore. A patient transport system is provided in general longitudinal alignment with the bore. The transport system is capable of retrievably positioning the patient volume in the active region of the magnetic field. The patient alignment system includes first and second assemblies for projecting first and second visible patterns on the surface of the patient. The second pattern is movable vertically within a predetermined range relative to a fixed reference point. Each of the assemblies includes means for sensing the position of the respective pattern. A control means is provided in signal communication with each of the means for sensing pattern position. The control means is responsive to the position of at least one of the patterns for controlling at least one parameter related to the NMR data.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

FIG. 5 is a block diagram schematic of an NMR system;

FIG. 6 is a block diagram schematic of the control system utilized with the patient alignment system in accordance with the invention.

DETAILED DESCRIPTION OF THE INVENTION

Figure 1:
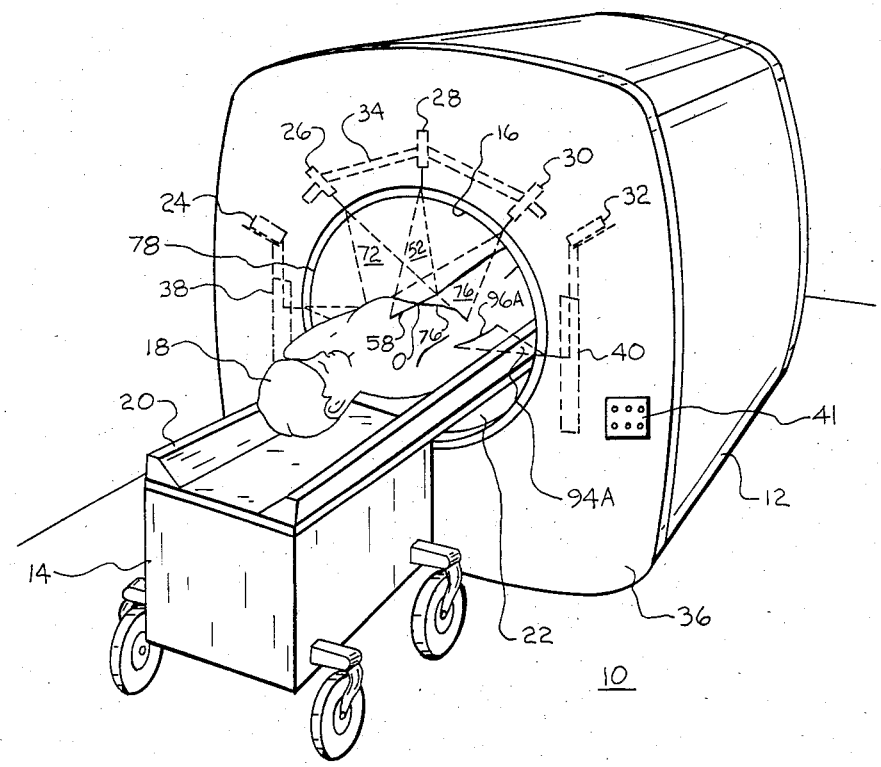
FIG. 1 is a perspective view of an NMR system including a schematic representation of the inventive patient alignment system.

Referring first to FIG. 1, there is shown a whole-body NMR scanning system generally designated 10 which includes a magnet 12 and a mobile patient transport table 14 which in operation is securely docked by means of a docking mechanism (not shown) with the magnet. Magnet 12 (equipped with RF and gradient coils) is provided with a bore 16 having a useful diameter of approximately 55 cm. sufficient to accommodate patient 18 shown in a supine position supported by a patient cradle 20. The cradle is provided with a set of rollers (not shown) for translating the patient into the magnet bore. A reversible longitudinal drive system (not shown) for moving the cradle and an encoder (not shown) for sensing cradle longitudinal position are provided in table 14. Within the bore there is provided a bridge 22 for supporting the weight of the patient and the cradle. The patient is shown in a feet-first orientation. However, the patient can be positioned in either the head-first or the feet-first orientation depending upon the area of the patient to be studied. For example, head studies are made with the patient in the head-first orientation; while lower chest and abdominal studies are preformed with the patient in the feet-first orientation.

The NMR system also includes a plurality of laser light sources 24, 26, 28, 30, and 32 mounted in a radial orientation on a magnet frame 34. The radial orientation is preferred since the laser bodies align with the magnetic flux lines minimizing distortion of laser optical elements thereby enabling normal laser operation. In the preferred embodiment, the lasers are of the helium-neon type having an output in the visible optical range with a pulsed power rating of about 1 milliwatt. The frame and the light sources are shown in FIG. 1 in phantom as being located behind a magnet front cover 36. Light sources 24 and 32, situated on either side of cradle 20, have associated therewith lateral support assemblies 38 and 40, respectively, which enable an optical assembly (not shown in FIG. 1) to travel in a vertical direction thereby to vary the position of a lateral alignment beam (e.g., 94A) on the patient. For illustration, light sources 24 and 32 are both shown as being energized; however, in operation, only one is used at a time. A remote operator control panel 41 is provided on the magnet front cover. The control panel is used to align the patient and to control other functions, as will be described hereinafter.

Figure 3:
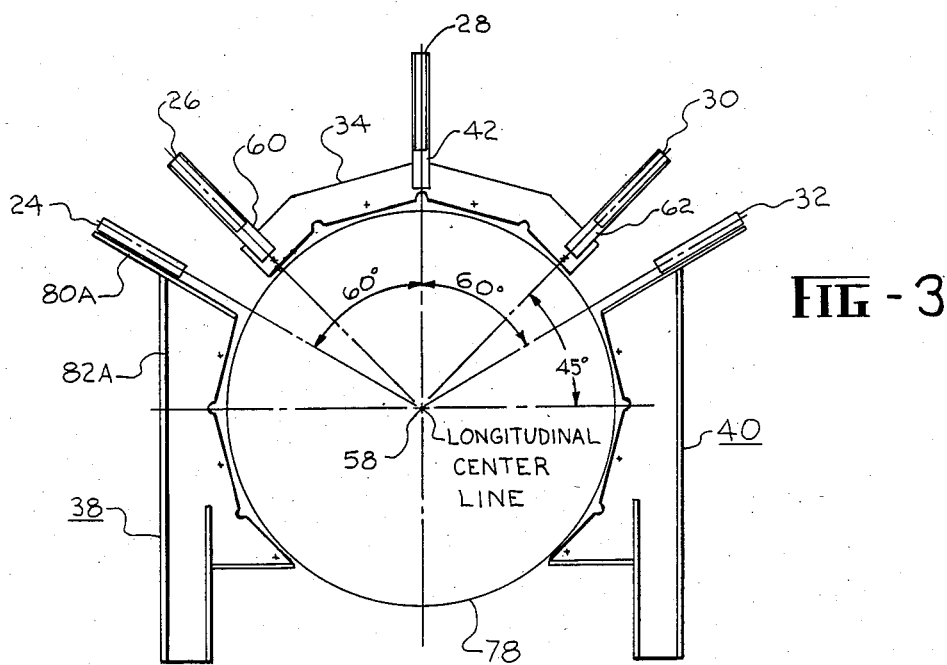
FIG. 3 is a front elevation view of the inventive patient alignment system.

The detailed structure of the fixed laser sources 26, 28, and 30 used in the patient alignment system will now be described with initial reference to FIGS. 1, 2, and 3. Light source 28 is mounted vertically over patient 18 in a bracket 42 secured to magnet frame 34. Source 28 produces a point source of light energy 44 which is guided by 45° mirrors 46 and 48 to a dispersing lens 50 having a series of small diameter cylindrical glass rods for projecting a fan beam of light generally designated 52. The light beam, which is bounded at its peripheries by rays 54 and 56, passes through an opening 49 in magnet cover 78 and strikes the upper surface of patient 18 and manifests itself as a visible line 58A which is coincident with a reference axis termed the longitudinal center line 58. Light sources 26 and 30 are mounted in brackets 60 and 62 in fixed positions along magnet frame 34 displaced by 45° on either side of source 28. The means by which the fan beam produced by each of sources 26 and 30 is identical to that already described with reference to source 28. However, for purposes of illustration, the optical elements associated with source 26 will be described using reference numerals having a suffix "A", while the identical counterparts associated with light source 30 are identified in FIG. 2 by like reference numbers having a "B" suffix. A point source of light 64A emanating from source 26 is deflected first by a 45° mirror 66A to a second 45° mirror 68A and then to a dispersing lens 70A. The resulting fan beam, generally designated 72, passes through an opening 69A in magnet cover portion 78 and impinges the upper surface of patient 18 in a direction perpendicular to that of fan beam 52 where it manifests itself as a visible line 76. In a similar manner, light source 30 produces a fan beam 74 the profile of which on the upper surface of the patient is coincident with that produced by fan beam 72. Visible lines 58A and 76 intersect at an optical reference point designated by the letter "O" which may be positioned over a distinctive anatomical patient landmark. The particular landmark over which the cross hairs are centered in FIG. 1 is the sternal notch. Anatomical landmarks are used in NMR as references for precisely locating the areas to be studied. Other commonly used landmarks are lower costal margin, external auditory meatus, and the iliac crest to cite a few examples.

The patient is positioned in FIG. 1 in what will be referred to as staged position of the NMR system. The purpose is to align an anatomical landmark with optical reference point "O". This is accomplished by adjusting the longitudinal position of cradle 20. The aligned position of the cradle is sensed by an encoder (not shown), or other suitable means such as a potentiometer. The encoder is located in the cradle and is coupled to the patient transport mechanism. The position is recorded as a reference point in a main computer (FIG. 6). Thereafter, the reference point sensed by the encoder is used to determine, how far the patient must be transported to position the region to be studied within the homogeneous portion of the magnetic field. The reference is also used to calculate the offset distance from the reference point to the center of the patient volume to be imaged, for example. The patient transport system under the control of the system computer provided with the reference data is capable of performing automatically the translation of the cradle to the position of the scan.

To display reconstructed images of the anatomy of interest which are centered in a field of view, it is necessary to have a reference to an image center. The image center is not a fixed reference point because of varying patient sizes such as, for example, infants and adults. The manner in which light sources 24 and 32 are utilized to provide such a reference will now be described with reference to FIGS. 1, 2, and 4.

Figure 2:
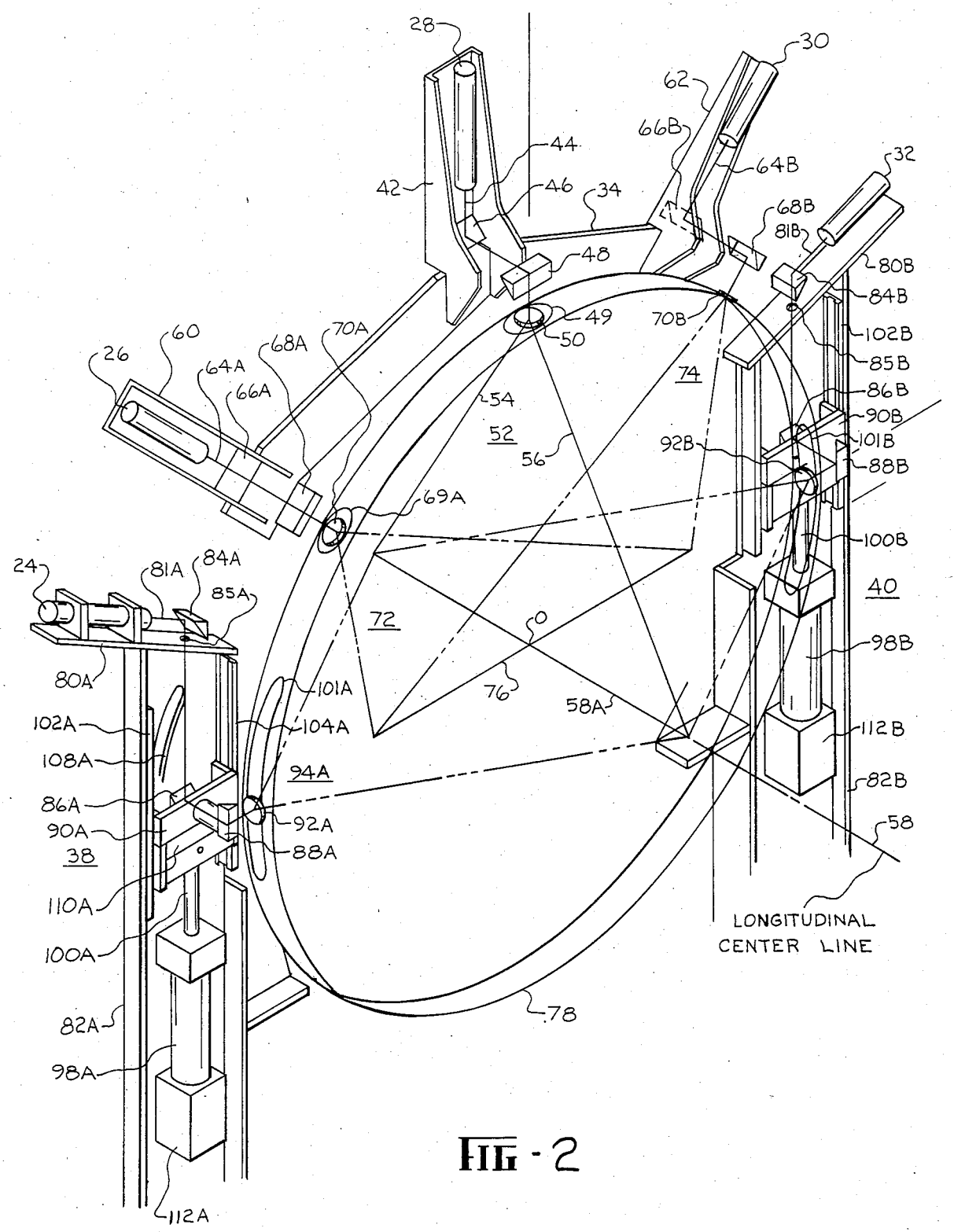
FIG. 2 is a detailed perspective view of the patient alignment system in accordance with the invention.
Figure 4:
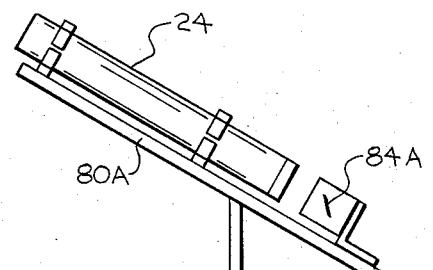
FIG. 4 is a front elevation view of one of the adjustable lateral laser assemblies utilized with the patient alignment system of the invention.

Referring to FIGS. 1, 2, and 4, light sources 24 and 32 and support assemblies generally designated 38 and 40 are positioned to the left and to the right sides, respectively, of patient 18 behind magnet front cover 36. Description will be made of only one of the light sources and support assemblies utilizing reference numerals having a suffix "A". Similar elements associated with light source 32 and slide assembly 40 have like reference numerals bearing a letter "B" suffix.

Continuing with reference to FIGS. 1, 2, and 4, light source 24 is mounted on a bracket 80A at an angle of 60° from vertical. Bracket 80A is mounted on vertical support member 82A. A first 45° mirror 84A is mounted on bracket 80A for deflecting light beam 81A emanating from source 24 through an aperture 85A in a direction parallel to support member 82A. A pair of additional 45° mirrors 86A and 88A mounted on a horizontal slide assembly 90A then deflect the light beam toward dispersion lens 92A which produces a fan beam 94A passing through an opening 101A formed in magnet cover portion 78 and lying in a horizontal plane (also referred to as the coronal plane). As best seen in FIG. 1, the fan beam impinges the side of patient 18 along a line 96A. The vertical position of line 96A is adjustable by means of a hydraulic cylinder 98A having a piston rod 100A which acts on the horizontal support 90A having its ends slidably captured in vertical track assemblies 102A and 104A. A hydraulic cylinder is preferred, rather than an electric motor, because of adverse effects of magnetic field on motor operation. As the piston rod moves the horizontal slide support up or down, as suggested by the bidirectional arrow C in FIG. 4, optical assembly 106A containing mirrors 86A, 100A, and lens 92A follows a curved cam track 108A which parallels magnet cover 78. Vertical motion along cam 108A causes lens 92A to move back and forth horizontally as indicated by bidirectional arrow D in FIG. 4 along a horizontal slide 110A. In this manner, lens 92A tracks the contour of magnet cover 78 thereby varying vertically the position of line 96A on the patient surface. The range of travel of lens assembly 106A is about 25 cm. above the longitudinal center line and about 10 cm. below. The vertical position of beam 94A is sensed by a conventional incremental encoder (or other suitable means such as a potentiometer) located in housing 112A (FIG. 2). The encoder follows the movement of piston rod 100A and its output is used as a reference in the image reconstruction process.

It will be recognized by those skilled in the art that the invention may be practiced other than as disclosed. For example, a single light source may be used with optical fiber cable to provide a point light source for the dispersing lenses to generate the fan beams. Similarly, a light source other than a laser may also be employed (e.g., an incandescent light source with light collimators).

The manner in which the information of the longitudinal position of the cradle, as determined by the use of laser lights 26, 28, and 30, and the information regarding the vertical position of fan beam 94A and measured by one of the encoders associated with light sources 24 and 32 is used will be described with reference to FIG. 6. However, it will be advantageous to consider first the overall NMR system configuration which will be disclosed next with reference to FIG. 5.

FIG. 5 depicts in block diagram form the major components of an NMR system. Overall system operation is under the control of a computer system generally designated 200 which includes a main computer 201 (such as a Data General MV4000). The computer has associated therewith an interface 202 through which a plurality of computer peripheral devices and other NMR system components are coupled. Among the computer peripheral devices is a magnetic tape drive 204 which may be utilized under the direction of the main computer for archiving patient data and images to tape. Processed patient data may also be stored in an image disc storage device designated 210. An array processor 206 is utilized for pre-processing of data and data reconstruction. The function of image processor 208 is to provide interactive image display manipulation such as magnification, image comparison, and gray scale adjustment. The computer system is provided with a means to store raw (unreconstructed) image data utilizing a disc data storage system designated 212. A main operator console 216 is also coupled to the computer by means of interface 201 and provides the operator with the means to input data pertinent to a patient study as well as additional data necessary for proper NMR system operation, such as initiating and terminating scans. The operator console may also be used to display images stored on discs or magnetic tape.

The computer system exercises control over the NMR system by means of control and gradient amplifier systems generally designated 218 and 228, respectively. The computer communicates with system control 218 by means of a digital communication network 203 (such as the Ethernet network) in a manner well known to those skilled in the art. The system control includes several subsystems such as the pulse control module (PCM) 220, a radio-frequency transceiver 222, a status and control module (SCM) 224, and the power supplies generally designated 226 necessary to energize the components. The pulse control module utilizes computer control signals to generate digital timing and control signals such as the current wave shapes that are used for gradient coil excitation as well as RF envelope waveforms utilized by the transceiver for modulating of RF pulses. The gradient wave shapes are applied to the gradient amplifier system generally comprised of amplifiers 230, 232, and 234, each utilized to excite a corresponding gradient coil in an assembly generally designated 236 and which is part of a magnet assembly 246. When energized, the gradient coils generate substantially linear, mutually orthogonal magnetic-field gradients $G_x$, $G_y$, and $G_z$ directed in the X-, Y- and Z-axis directions of a Cartesian coordinate system. The point of intersection defined by the planes containing each of the gradients is termed an "isocenter" and normally is situated substantially at the center of the static magnetic-field volume. The reconstructed images are typically centered at the isocenter. The gradients are utilized in combination with radio-frequency pulses generated by transceiver 222 to encode spatial information into the NMR signals emanating from the region of the patient being studied. Waveforms and control signals provided by the pulse control module are utilized by transceiver subsystem 222 for RF carrier modulation and control of the operating mode; that is, the transmit or receive mode. In the transmit mode, the transmitter provides a radio-frequency carrier waveform modulated in accordance with the control signals provided by the pulse control module to an RF amplifier 223 which then energizes RF coils 238 which are situated within main magnet assembly 246. The NMR signals radiated by the excited nuclei are sensed by the same or a different RF coil than is used for transmitting. The signals are detected, filtered, and digitized in the receiver section of the transceiver. The digitized signals are transmitted to the main computer for processing through interface 202 by means of a dedicated, unidirectional, high-speed digital link 205.

The PCM and SCM are independent subsystems both of which communicate with main computer 201, peripheral systems, such as patient positioning system 252, as well as to one another by means of link 203. The PCM and SCM are each comprised of a 16-bit microprocessor (such as an Intel 8086) for processing commands from the main computer, as will be described with reference to FIG. 6. The SCM includes means for acquiring information regarding cradle position and position of the moveable patient-alignment fan beam. This information is used by the main computer to modify image display and reconstruction parameters (such as offset). The SCM also initiates functions such as actuation of the patient transport and laser systems.

The gradient coil assembly 236 and the RF transmit and receiver coils 238 are mounted within the bore of the magnet utilized to produce the polarizing magnetic field. The magnet forms a part of the main magnet assembly which includes the patient alignment system 248, a shim coil power supply 240, and a main magnet power supply 242. The shim power supply is utilized to energize shim coils associated with the main magnet and which are used to correct inhomogeneities in the polarizing magnetic field. In the case of a resistive magnet, main magnet power supply 242 is utilized to continuously energize the magnet. In the case of a superconductive magnet, the power supply is utilized to bring the magnet to the proper operating field and then is disconnected. The patient alignment system 248 operates in combination with a patient cradle and transport system 250 and patient positioning system 252. To minimize interference from external sources, the NMR system depicted in FIG. 1 comprised of the main magnet assembly, the gradient coil assembly, and the RF transmit and receiver coils, as well as the associated power supplies and patient-handling devices, are enclosed in an RF-shielded room generally designated 244. The shielding is generally provided by a copper or aluminum screen network which encloses the entire room. The screen room serves to contain the RF signals generated by the system while shielding the system from RF signals generated outside the screen room. A bidirectional attenuation of approximately 100 db. is typical in the frequency range of operation. The status and control module 226, and the other subsystems ensure the overall system integrity. The function of the status and control module as it applies to the patient alignment system will be described next with reference to FIG. 6.

Referring now to FIG. 6, there is shown the status and control module (SCM) 224 coupled as described hereinbefore to the main computer by means of communication link 203. The SCM has also coupled to it tableside control panel such as that designated 41 which is also shown on the front magnet cover 36 in FIG. 1. There may be more than one set of table-side controls; for example, one on each side of the patient cradle. Upon reception of a control signal either from the table-side control panel or from the main operator console, the SCM transmits a laser-enable signal to patient positioning system 252 which them activates one of laser light sources 24 and 32. Similarly, the laser-enable signal is used to activate fixed beam sources 26, 28, and 30. Typically, it is desirable to first activate sources 26, 28, and 30 such that output optics 50 and 70 generate fan beams 52 and 72 which display the optical alignment point O on the top surface of the patient. Point O is aligned with a selected patient anatomical feature by moving patient cradle 20 either manually or with the aid of a reversible table drive which forms part of patient cradle and transport system 250. Following the alignment, the position of the cradle is sensed by an encoder 264, which is part of patient positioning system 252, and is transmitted to the SCM and from there by means of the digital communication link to the main computer. The main computer utilizes this information to provide the necessary commands to the PCM module 220 to generate the correct waveforms for driving the gradient and RF coils. The computer also provides information to the PCM to properly select an operation state for the transceiver 222 as described hereinbefore. The information from encoder 264 is also used to specify the position of the first scan and any additional scan relative to the anatomical reference feature selected. The scanning function is performed automatically under the control of the main computer through the PCM and SCM modules.

Table-side control panel 41 may also be utilized to activate a reversible drive 98 (hydraulic cylinder 98A and piston rod 100A, FIG. 2) which is used to control the vertical position of the light beam generated by optical source 24 (or 32). The vertical position of the lateral beam 94A on the patient is sensed by an encoder 262 and transmitted to the patient positioning system and from there to the SCM and the main computer. With this reference information the computer can then generate the needed commands to execute the desired function.

The information of the vertical position of the lateral beam produced by either source 24 or 32 can be used for several purposes. The information can be used to provide a reference position which is used to reconstruct centered images, the information can also be used to adjust the bandwidth of a conventional programmable bandpass filter in the transceiver system 222 (FIG. 5) to improve image signal-to-noise ratio (S/N). Additionally, the information can be used to perform offset scans.

Figure 7:
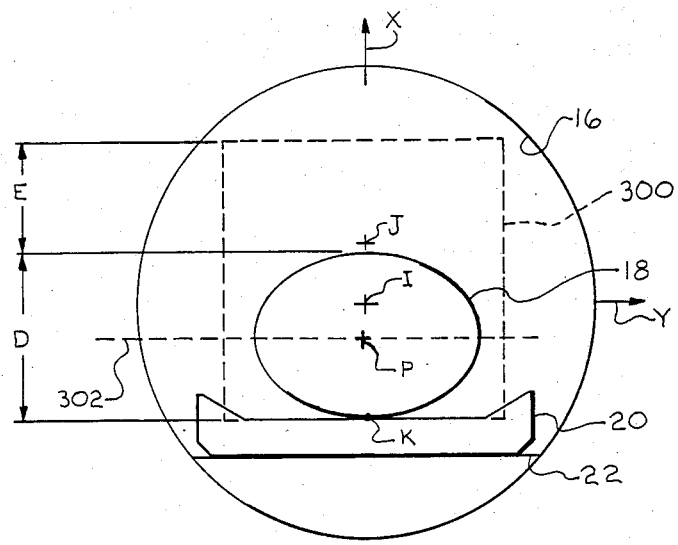
FIGS. 7 and 8 are cross-sectional views of the NMR system.

The use of the information for reconstructing centered images will now be described with reference to FIG. 7, which depicts a cross-sectional view of magnet bore 16. Patient 18 (seen in cross section) is positioned in the bore on cradle 20 supported by bridge 22. The patient cross section is positioned asymmetricaly relative to the isocenter designated I. Unless an adjustment is made, the reconstructed image will appear off center in the field of view 300 shown superimposed by dash lines in FIG. 7. A centered image can be reconstructed by providing a new reference point P centered in the patient region to be imaged. This can be accomplished by measuring distance D (using one of the beams produced by laser sources 24 or 32) between a fixed reference point such as the cradle top and the top surface of the patient. One half of distance D represents the midcoronal plane (rising out of the plane of the figure as indicated by dashed line 302 passing through point P). The distance (e.g., in centimeters) between isocenter I and patient center P can be determined given that the height of both points above the cradle is now known. The position of points not centered on line 302 can be determined by aligning the laser beam vertically with the level of the new point of interest and subtracting that from distance D. One method of reconstructing or displaying offset images which are centered in the field of view is to determine the amount of frequency offset due to the fact that the center of the region of interest is spatially displaced from the isocenter.

The frequency offset can be determined by considering a concrete example of a known imaging technique such as the spin-warp version of Fourier transform imaging. A substantially linear magnetic-field gradient $G_x$ (with an amplitude measured in gauss/centimeter) is typically applied in the X-axis direction to introduce frequency/position dependence into the NMR signal. The frequency dependence is due to the Larmor equation $\omega = \gamma B$, where $\omega$ is the resonant frequency, $\gamma$ is the gyromagnetic ratio, and B (polarizing field and gradient) is the strength of the applied magnetic field. The field of view has, therefore, associated therewith (in the direction of the gradient) a frequency bandwidth BW with the isocenter I having a known center frequency. If the reconstructed image is to have 128 pixels (image elements), then field of view in the direction of $G_x$ gradient can be divided into 128 frequency increments having the dimensions of Hz/cm. (BW/size in centimeters of field of view). The frequency offset associated with point P (which is to be the center of the image) can be determined by multiplying the distance in centimeters between point I and P by the frequency increment Hz/cm. The frequency thus obtained is then added to the center frequency associated with point I (corresponding to the isocenter) to obtain the frequency at point P. A centered image is reconstructed using point P as the new reference in the reconstruction process.

An image having an improved S/N can be reconstructed if the NMR signal is filtered to remove those signal frequencies which do not contribute to the image but which contribute to image noise. One example where it would be advantageous to adjust the filter bandwidth is shown in FIG. 7. The region in the field of view 300 having a width E does not contain image information and could be removed by narrowing the bandwidth of the programmable bandwidth filter in transceiver 222 (FIG. 5). This can be accomplished by determining the frequency associated with a point J (FIG. 7) using the lateral laser beam in the manner disclosed hereinabove. This information is then used to adjust the filter bandwidth and image center frequency to pass substantially only the frequencies lying between point J and K on either side of the patient, thereby limiting noise contributions from noise sources with frequencies outside of the frequency covered by the patient. The adjustment of the filter bandwidth is also beneficial in eliminating aliasing artifacts.

Figure 8:
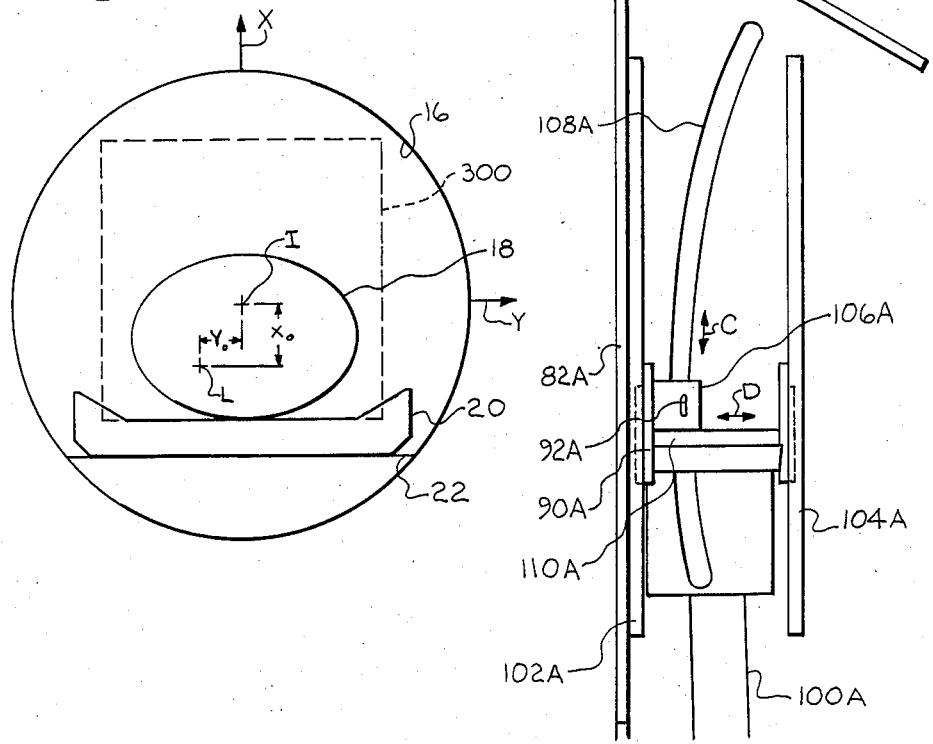

It is desirable at times to reconstruct an image centered on point L shown in FIG. 8 which is selected to be coincident with an anatomical feature of interest. One way this can be accomplished in an existing image data array is to specify from the operator console a new image center using pixel coordinates in the pixel data array coincident with point L. The number of pixels by which points L is offset from the isocenter in the X- and Y-axis direction is used to offset the image data to display a centered image. The array may typically comprise 128×128, 256×256, or 512×512 image pixels. This procedure involves the retrospective manipulation of existing image data.

Another way in which the image center can be offset is to prospectively specify the coordinate offsets ($X_o$, $Y_o$) needed to center the image at point L before making the scan. The $X_o$ offset is determined using one of light sources 24 or 32 as described with reference to FIG. 7 for point P. The $Y_o$ offset requires that beam 52 (FIG. 2) produced by laser source 28 to be movable (not shown) such that the position of visible line 58A (and, hence, point O) is adjustable. This can be achieved by providing source 28 with an assembly, such as 38 or 40, for adjusting beam position. The assembly would, of course, include a hydraulic cylinder and piston rod, as well a position-sensing encoder. The offset along the X axis typically (direction of gradient $G_x$) indicates a frequency offset from the center frequency associated with isocenter I. In practice, the $X_o$ offset is the amount by which the conventional center frequency of the receiver in transceiver 222 is offset so as to be centered on a new center frequency. The $Y_o$ offset is indicative of the phase offset (in the spin-warp method) from the known phase associated with the isocenter. The phase offset is determined in the same manner as the frequency offset. A $G_y$ gradient (applied along the Y-axis direction) having programmable duration and amplitude products is applied to encode phase/position information across the field of view. The phase bandwidth is treated in the same manner as the freqnecy bandwidth to determine the $Y_o$ offset. The $Y_o$ offset is utilized to provide a complex modulation function for radio-frequency pulses used to excite nuclear spins in the object region of interest. The manner in which the $X_o$ and $Y_o$ offsets are used to reconstruct magnified images centered at point L is disclosed and claimed in the aforeidentified patent application. Of course, the offsets can also be utilized to reconstruct unmagnified offset images. Unlike magnified images, which require larger gradient amplitudes, unmagnified images do not require modification of gradient amplitudes.

It will be appreciated from the foregoing that in accordance with the invention there is provided a patient alignment system capable of providing patient position information useful in NMR studies. The information is used for precisely positioning the patient within the magnetic field volume having optimum homogeneity. The information provided is also useful in reconstructing centered images even when the region of interest is not centered with the isocenter. Patient position information is used to determine the dimension and location of the patient region to be studied.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

What is claimed is:

1. A patient alignment system useful with an NMR system for acquiring NMR data in the course of a scan of a predetermined volume of a patient, the NMR system including a magnet for producing a polarizing magnetic field within a magnet bore sized for receiving the patient volume, and a patient transport system in general longitudinal alignment with the magnet bore capable of positioning the patient volume for scanning in an advanced position in the active region of the magnetic field centered approximately at the isocenter and for retrieving the patient volume to a staged position substantially out of the active region of the magnetic field, the patient alignment system comprising:

a first assembly including at least one energy source capable of projecting in use a first visible pattern on the surface of a patient;

first means for detecting the position of the patient transport system when said first visible pattern is aligned with a patient anatomical reference point in the staged position prior to performing the NMR scan;

a second assembly including at least one energy source means capable of projecting in use a second visible pattern lying substantially in a horizontal plane on a surface of a patient, said second assembly including means for varying in use within a predetermined range the vertical position relative to the horizontal plane of said second visible pattern with respect to a fixed reference point;

second means for detecting the position of said second visible pattern on the patient surface; and control means in signal communication with said first and second means for detecting, said control means being responsive to the position of at least one of the first and second visible patterns for controlling at least one parameter used for altering at least one of NMR data acquisition, image reconstruction and display.

2. The patient alignment system of claim 1 wherein said control means is responsive to said first means detecting for the distance between the isocenter and the center of the patient volume of interest so as to position the patient volume substantially in the active magnetic field region for scanning.

3. The patient alignment system of claim 1 wherein said control means is responsive to said second means for detecting the vertical distance between said fixed reference point and the position of said second pattern.

4. The patient alignment system of claim 1 wherein NMR data acquisition comprises acquisition of NMR image data from the predetermined patient volume, and wherein said control system is responsive to the position of at least one of said patient transport means and said second visible pattern to provide a reference which is offset relative to the isocenter of the NMR system, which reference is useful for formatting NMR images produced using said NMR image data.

5. The patient alignment system of claim 1 wherein each of said energy source means for projecting said first and second visible patterns comprises a laser.

6. The patient alignment system of claim 1 wherein said first assembly comprises a plurality of energy sources each having optical means for projecting a portion of said first visible pattern, said plurality of energy sources including a first source positioned generally vertically above the patient for projecting a longitudinal center line, and at least one source positioned at an angle relative to said first source for projecting a line transverse to said longitudinal center line, said lines defining said first visible pattern.

7. The patient alignment system of claim 1 wherein said second assembly comprises at least a first energy source including a first optical assembly for projecting a first portion of said second visible pattern, said first optical assembly being coupled to a piston rod of a first hydraulic cylinder to enable said first optical assembly for vertical movement thereby to vary the vertical position of said first portion of said second visible pattern.

8. The patient alignment system of claim 7 wherein said second means for detecting position comprises encoder means coupled to sense the position of said piston rod.

9. The patient alignment system of claim 7 wherein said second assembly further comprises a second energy source including a second optical assembly for projecting a second portion of said second visible pattern, said second optical assembly being coupled to a piston rod of a second hydraulic cylinder to enable said second optical assembly for vertical movement thereby to vary the vertical position of said second visible pattern portion, said first and second energy sources and said first and second optical assemblies associated therewith being disposed on either side of the patient transport system.

10. The patient alignment system of claim 6 wherein said first source comprises an optical assembly coupled to a piston rod of a hydraulic cylinder to enable said optical assembly for movement to vary the position of said longitudinal center line.

* * * * *